United States Patent
Koo et al.

(10) Patent No.: US 7,361,501 B2
(45) Date of Patent: Apr. 22, 2008

(54) MINIATURIZED SPECTROMETER USING OPTICAL WAVEGUIDE AND INTEGRATED RAMAN SYSTEM ON-CHIP

(75) Inventors: Tae-Woong Koo, Cupertino, CA (US); Richard Jones, Santa Clara, CA (US); Andrew A. Berlin, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 41 days.

(21) Appl. No.: 11/239,100

(22) Filed: Sep. 30, 2005

(65) Prior Publication Data

US 2007/0077595 A1    Apr. 5, 2007

(51) Int. Cl.
*C12M 3/00*    (2006.01)
(52) U.S. Cl. .................................. 435/287.2
(58) Field of Classification Search ............. 435/287.2, 435/4; 356/346
See application file for complete search history.

(56) References Cited

U.S. PATENT DOCUMENTS 5,909,280 A * 6/1999 Zavracky ................... 356/454

6,900,895 B2 * 5/2005 Van Wiggeren ............ 356/477

* cited by examiner

*Primary Examiner*—Ann Y. Lam
(74) *Attorney, Agent, or Firm*—Darby & Darby, PC

(57) ABSTRACT

One embodiment relates to an analyzer having an interferometer, a detector and a microprocessor, wherein the analyzer does not contain a spectrometer having a dispersive grating, the interferometer is to create a phase shift in an original spectrum of electromagnetic radiation emitted from a sample and Fourier transform the original spectrum to a Fourier transform spectrum, the detector is to detect a characteristic of the Fourier transform spectrum, and the microprocessor comprises software or a hardware to inverse transform the Fourier transform spectrum and reproduce the original spectrum. Another embodiment relates to a Raman analyzer having an interferometer, wherein the Raman analyzer contains no dispersive grating or moving parts and has an ability to analyze a Raman signal. The embodiments of the invention could be used for analyzing a sample by striking a laser to the sample and examining the spectrum of the emitted electromagnetic radiation from the sample.

20 Claims, 10 Drawing Sheets

FIG. 3
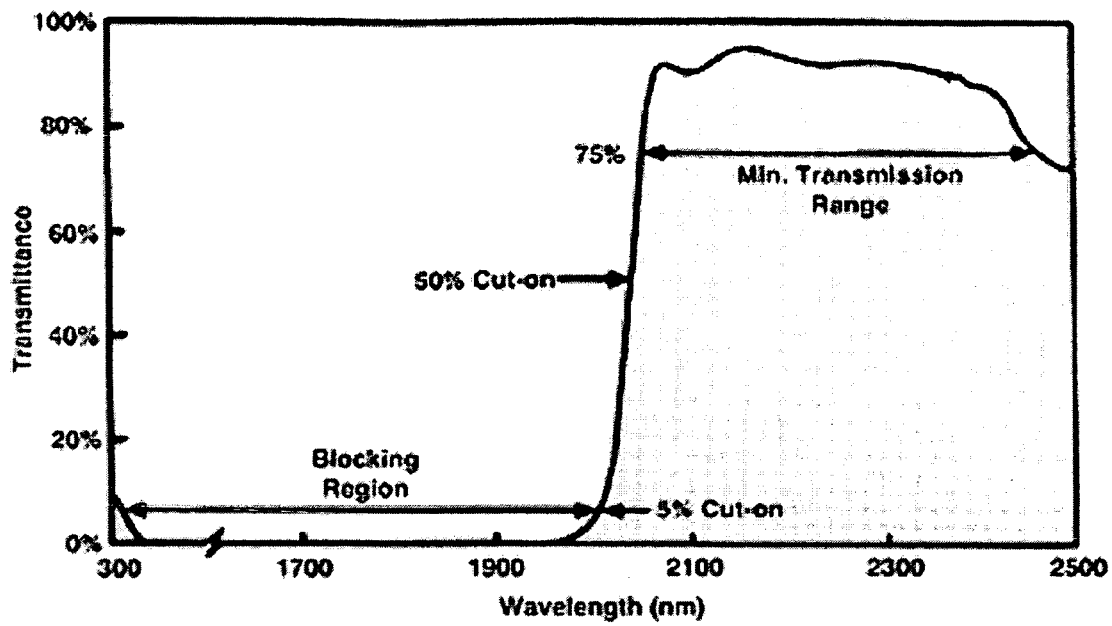
Long Wave Pass
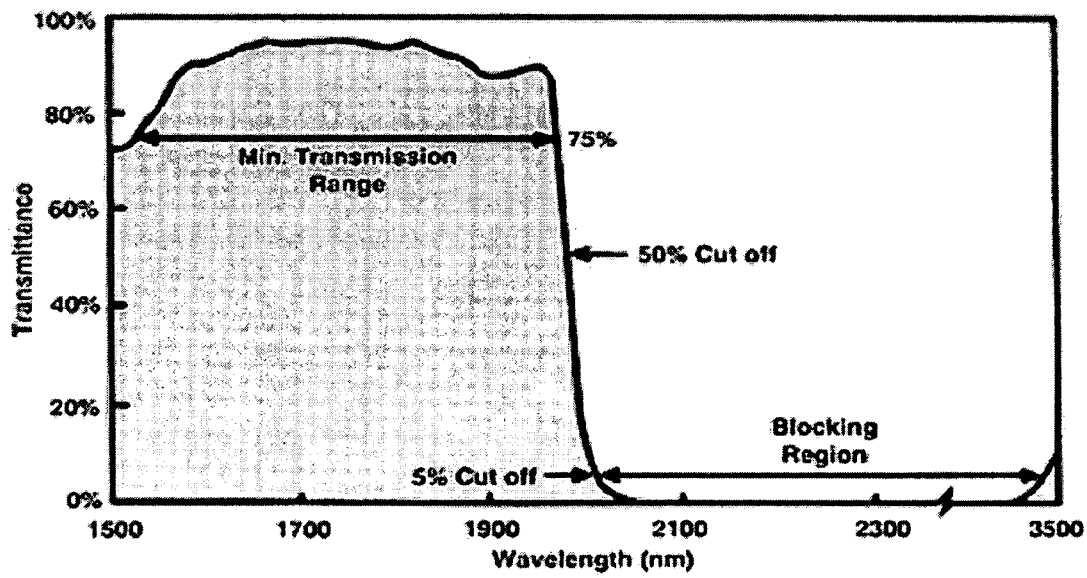
Short Wave Pass

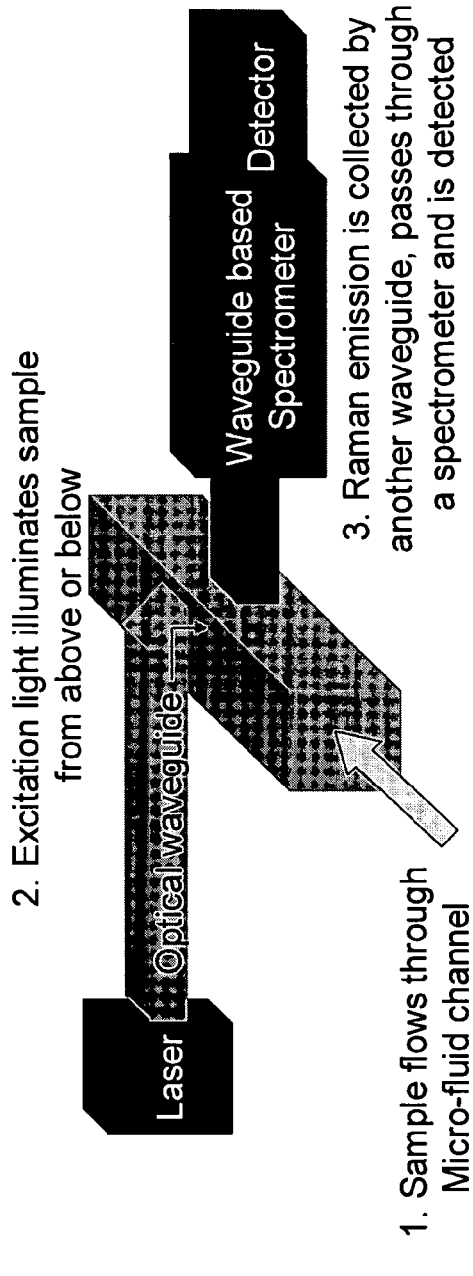
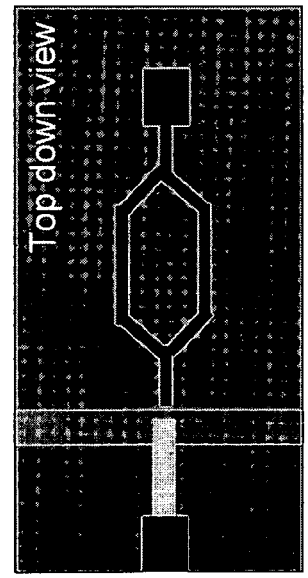
FIG. 7

FIG. 8

Raman-on-chip
Specific embodiment
2. micro-array based system, sample prep 1. On a substrate coated with capture molecules, introduce the sample and the labeled probe molecules.

2. A capture molecule, a target molecule in the sample, and a labeled probe molecule form a complex.

Probe molecules with COIN label

Target molecules in the sample

Substrate coated with capture molecules

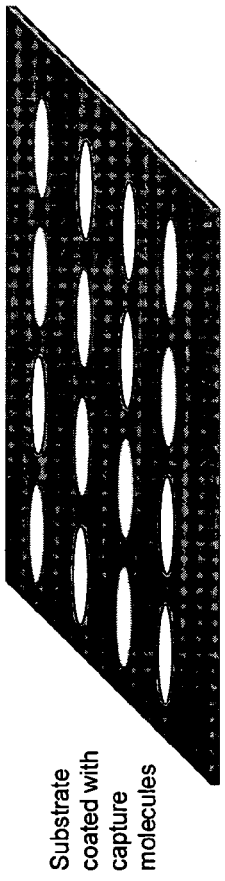
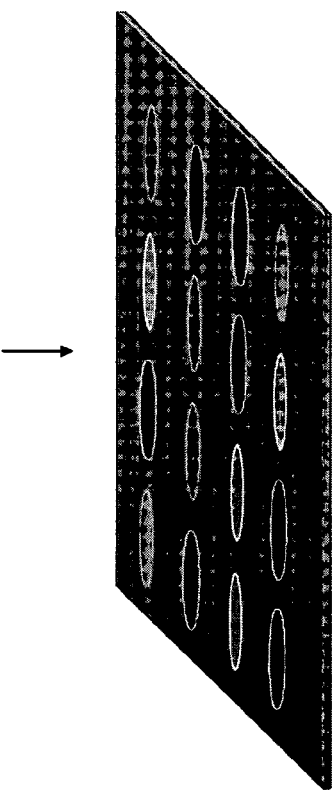

MINIATURIZED SPECTROMETER USING OPTICAL WAVEGUIDE AND INTEGRATED RAMAN SYSTEM ON-CHIP

RELATED APPLICATIONS

This application is related to U.S. application Ser. Nos.: (1) 11/026,857, filed Dec. 30, 2004, (2) 10/916,710, filed Aug. 11, 2004, (3) 11/027,470, filed Dec. 30, 2004, (4) 10/927,996, filed Aug. 26, 2004, (5) 10/940,698, filed Sep. 13, 2004, (6) 10/748,336, filed Dec. 29, 2003, and entitled "Method and instrument for collecting Fourier transform (FT) Raman spectra for imaging applications," filed herewith, which are incorporated herein by reference.

FIELD OF INVENTION

The embodiments of the invention relate to a miniaturized device that can analyze the intensity of input light as a function of wavelength, e.g., a spectrometer, and a method of using a miniaturized interferometer, e.g., as a spectrometer. The embodiments also relate to an integrated device for Raman spectroscopy. The invention transcends several scientific disciplines such as polymer chemistry, biochemistry, molecular biology, medicine and medical diagnostics.

BACKGROUND

An optical spectrometer is a device that can analyze the incoming light by frequency (wavelength) components and their intensities. In general, there are two types of spectrometers: dispersive and interferometric. A dispersive spectrometer has an optically dispersive component (e.g. prism or grating) to spatially disperse the incoming light as a function of wavelength. The dispersed light is collected by multi-channel detectors. An interferometric spectrometer records the interference pattern generated by the incoming light, and mathematically converts the interference pattern to a spectrum. An example of an interferometric spectrometer is a Fourier-transform infrared spectrometer (FTIR) based on a Michelson interferometer (FIG. 1).

The current spectrometers have two limitations for use in home and field applications such as for medical diagnosis. First, the size of the spectrometer (spectrometer as a component of a spectroscopy system) is too big. Typical spectrometers are bench-top models. Even the "portable" spectroscopic systems are toolbox or briefcase size. Thus, the current spectrometers are too big to be used in field applications or at home environment. Second, the cost of typical spectroscopy systems is more than $100,000. Thus, there is a need for a miniaturized, preferably hand-held approximately palm-size, spectrometers.

BRIEF DESCRIPTION OF THE DRAWINGS

FIG. 3 shows the transmission spectra of long and short wave pass edge filters.

FIG. 7 shows the detection methodology for a micro-fluid channel based MZI or ROC analyzer systems.

FIG. 8 shows the sample preparation method for a micro-array based MZI or ROC analyzer systems.

DETAILED DESCRIPTION

Figure 1:
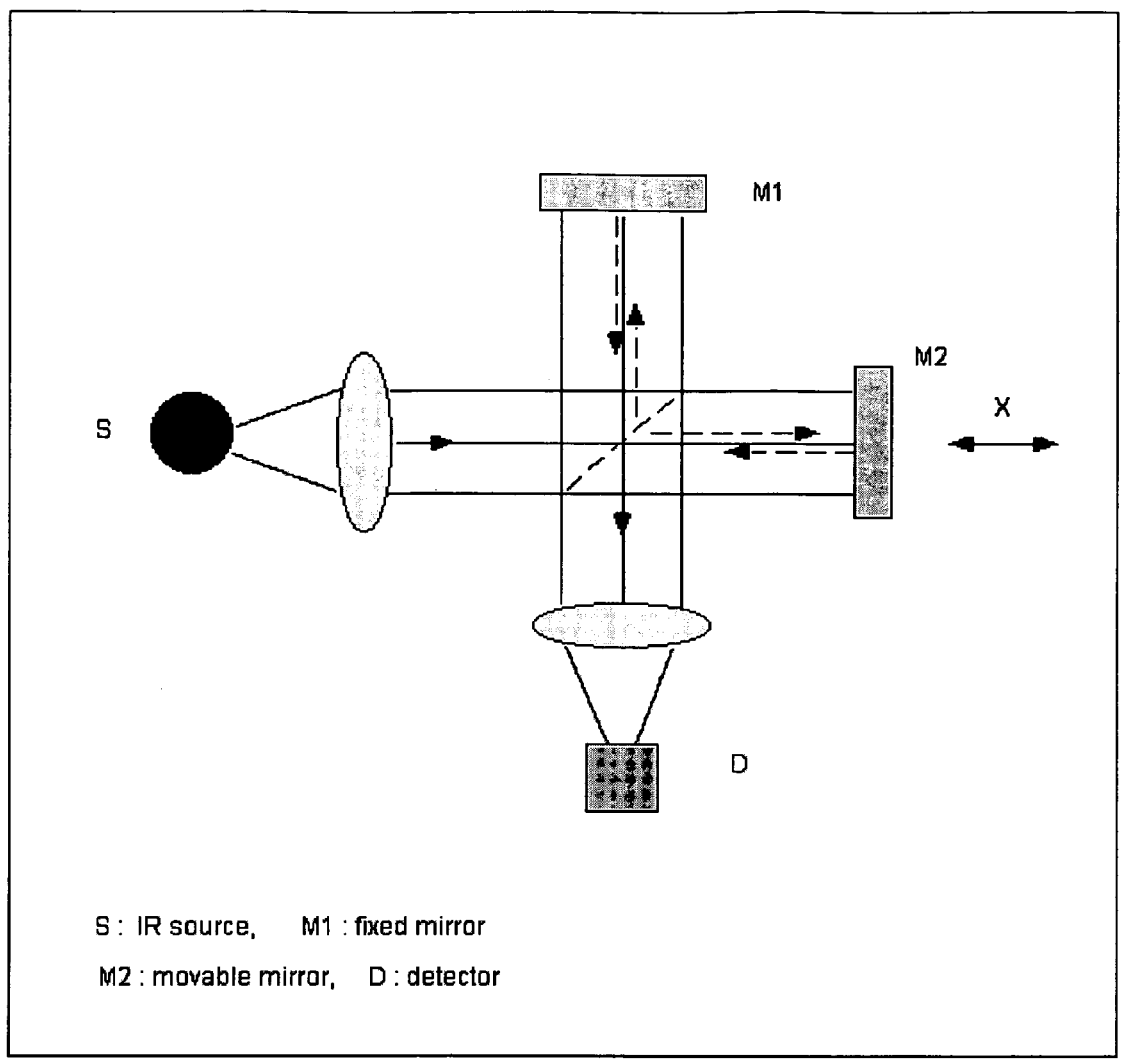
FIG. 1 shows a Fourier-transform infrared spectrometer (FTIR) based on Michelson interferometer.

As used in the specification and claims, the singular forms "a", "an" and "the" include plural references unless the context clearly dictates otherwise. For example, the term "an array" may include a plurality of arrays unless the context clearly dictates otherwise.

An "array," "macroarray" or "microarray" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "target" or "target molecule" refers to a molecule of interest that is to be analyzed, e.g., a nucleotide, an oligonucleotide, or a protein. The target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target molecule may be fluorescently labeled DNA or RNA.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the substrate of the array. The probe or probe molecule is typically a nucleotide, an oligonucleotide, or a protein, including, for example, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

The term "capture molecule" refers to a molecule that is immobilized on a surface. The capture molecule is generally, but not necessarily, binds to a target or target molecule. The capture molecule is typically a nucleotide, an oligonucleotide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. The capture molecule may be fluorescently labeled DNA or RNA. The capture molecule may or may not be capable of binding to just the target molecule or just the probe molecule.

The terms "die," "polymer array chip," "DNA array," "array chip," "DNA array chip," or "bio-chip" are used interchangeably and refer to a collection of a large number of probes arranged on a shared substrate which could be a portion of a silicon wafer, a nylon strip or a glass slide.

The term "chip" or "microchip" refers to a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components.

The term "molecule" generally refers to a macromolecule or polymer as described herein. However, arrays comprising single molecules, as opposed to macromolecules or polymers, are also within the scope of the embodiments of the invention.

"Predefined region" or "spot" or "pad" refers to a localized area on a solid support. The spot could be intended to be used for formation of a selected molecule and is otherwise referred to herein in the alternative as a "selected" region. The spot may have any convenient shape, e.g., circular, rectangular, elliptical, wedge-shaped, etc. For the sake of brevity herein, "predefined regions" are sometimes referred to simply as "regions" or "spots." In some embodiments, a predefined region and, therefore, the area upon which each distinct molecule is synthesized is smaller than about 1 cm$^2$ or less than 1 mm$^2$, and still more preferably less than 0.5 mm$^2$. In most preferred embodiments the regions have an area less than about 10,000 µm$^2$ or, more preferably, less than 100 µm$^2$, and even more preferably less than 10 µm$^2$ or less than 1 µm$^2$. Additionally, multiple copies of the polymer will typically be synthesized within any preselected region. The number of copies can be in the hundreds to the millions. A spot could contain an electrode to generate an electrochemical reagent, a working electrode to synthesize a polymer and a confinement electrode to confine the generated electrochemical reagent. The electrode to generate the electrochemical reagent could be of any shape, including, for example, circular, flat disk shaped and hemisphere shaped.

"Micro-Electro-Mechanical Systems (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

A "carbon nanotube" refers to a fullerene molecule having a cylindrical or toroidal shape. A "fullerene" refers to a form of carbon having a large molecule consisting of an empty cage of sixty or more carbon atoms.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including $\alpha$, $\beta$, or $\omega$-amino acids. When the amino acids are $\alpha$-amino acids, either the L-optical isomer or the D-optical isomer may be used. Additionally, unnatural amino acids, for example, $\beta$-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

The term "COIN" refers to a composite-organic-inorganic nanoparticle(s). The COIN could be surface-enhanced Raman scattering (SERS, also referred to as surface-enhanced Raman spectroscopy)-active nanoclusters incorporated into a gel matrix and used in certain other analyte separation techniques described herein. COINs are composite organic-inorganic nanoclusters. These SERS-active probe constructs comprise a core and a surface, wherein the core comprises a metallic colloid comprising a first metal and a Raman-active organic compound. The COINs can further comprise a second metal different from the first metal, wherein the second metal forms a layer overlying the surface of the nanoparticle. The COINs can further comprise an organic layer overlying the metal layer, which organic layer comprises the probe. Suitable probes for attachment to the surface of the SERS-active nanoclusters include, without limitation, antibodies, antigens, polynucleotides, oligonucleotides, receptors, ligands, and the like.

The metal required for achieving a suitable SERS signal is inherent in the COIN, and a wide variety of Raman-active organic compounds can be incorporated into the particle. Indeed, a large number of unique Raman signatures can be created by employing nanoclusters containing Raman-active organic compounds of different structures, mixtures, and ratios. Thus, the methods described herein employing COINs are useful for the simultaneous detection of many analytes in a sample, resulting in rapid qualitative analysis of the contents of "profile" of a body fluid. In addition, since many COINs can be incorporated into a single nanoparticle, the SERS signal from a single COIN particle is strong relative to SERS signals obtained from Raman-active materials that do not contain the nanoclusters described herein as COINs. This situation results in increased sensitivity compared to Raman-techniques that do not utilize COINs.

COINs could be prepared using standard metal colloid chemistry. The preparation of COINs also takes advantage of the ability of metals to adsorb organic compounds. Indeed, since Raman-active organic compounds are adsorbed onto the metal during formation of the metallic colloids, many Raman-active organic compounds can be incorporated into the COIN without requiring special attachment chemistry.

In general, the COINs could be prepared as follows. An aqueous solution is prepared containing suitable metal cations, a reducing agent, and at least one suitable Raman-active organic compound. The components of the solution are then subject to conditions that reduce the metallic cations to form neutral, colloidal metal particles. Since the formation of the metallic colloids occurs in the presence of a suitable Raman-active organic compound, the Raman-active organic compound is readily adsorbed onto the metal during colloid formation. COINs of different sizes can be enriched by centrifugation.

The COINs can include a second metal different from the first metal, wherein the second metal forms a layer overlying the surface of the nanoparticle. To prepare this type of SERS-active nanoparticle, COINs are placed in an aqueous solution containing suitable second metal cations and a reducing agent. The components of the solution are then subject to conditions that reduce the second metallic cations so as to form a metallic layer overlying the surface of the nanoparticle. In certain embodiments, the second metal layer includes metals, such as, for example, silver, gold, platinum, aluminum, and the like. Typically, COINs are substantially spherical and range in size from about 20 nm to 60 nm. The size of the nanoparticle is selected to be about one-half the wavelength of light used to irradiate the COINs during detection.

Typically, organic compounds are attached to a layer of a second metal in COINs by covalently attaching organic compounds to the surface of the metal layer Covalent attachment of an organic layer to the metallic layer can be achieved in a variety ways well known to those skilled in the art, such as for example, through thiol-metal bonds. In alternative embodiments, the organic molecules attached to the metal layer can be crosslinked to form a molecular network.

The COIN(s) can include cores containing magnetic materials, such as, for example, iron oxides, and the like such that the COIN is a magnetic COIN. Magnetic COINs can be handled without centrifugation using commonly available magnetic particle handling systems. Indeed, magnetism can be used as a mechanism for separating biological targets attached to magnetic COIN particles tagged with particular biological probes.

As used herein, "Raman-active organic compound" refers to an organic molecule that produces a unique SERS signature in response to excitation by a laser. A variety of Raman-active organic compounds are contemplated for use as components in COINs. In certain embodiments, Raman-active organic compounds are polycyclic aromatic or heteroaromatic compounds. Typically the Raman-active organic compound has a molecular weight less than about 300 Daltons.

Additional, non-limiting examples of Raman-active organic compounds useful in COINs include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2', 4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like.

In certain embodiments, the Raman-active compound is adenine, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, or 9-amino-acridine 4-amino-pyrazolo(3,4-d)pyrimidine, or 2-fluoroadenine. In one embodiment, the Raman-active compound is adenine.

When "fluorescent compounds" are incorporated into COINs, the fluorescent compounds can include, but are not limited to, dyes, intrinsically fluorescent proteins, lanthanide phosphors, and the like. Dyes useful for incorporation into COINs include, for example, rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-$Me_2$, N-coumarin-4-acetate, 7-OH-4-$CH_3$-coumarin-3-acetate, 7-$NH_2$-4$CH_3$-coumarin-3-acetate (AMCA), monobromobimane, pyrene trisulfonates, such as Cascade Blue, and monobromotrimethyl-ammoniobimane.

Multiplex testing of a complex sample would generally be based on a coding system that possesses identifiers for a large number of reactants in the sample. The primary variable that determines the achievable numbers of identifiers in currently known coding systems is, however, the physical dimension. Tagging techniques, based on surface-enhanced Raman scattering (SERS) of fluorescent dyes, could be used in the embodiments of this invention for developing chemical structure-based coding systems. The organic compound-assisted metal fusion (OCAM) method could be used to produce composite organic-inorganic nanoparticles (COIN) that are highly effective in generating SERS signals allows synthesis of COIN labels from a wide range of organic compounds to produce sufficient distinguishable COIN Raman signatures to assay any complex biological sample. Thus COIN particles may be used as a coding system for multiplex and amplification-free detection of bioanalytes at near single molecule levels.

COIN particles generate intrinsic SERS signal without additional reagents. Using the OCAMF-based COIN synthesis chemistry, it is possible to generate a large number of different COIN signatures by mixing a limited number of Raman labels for use in multiplex assays in different ratios and combinations. In a simplified scenario, the Raman spectrum of a sample labeled with COIN particles may be characterized by three parameters: (a) peak position (designated as L), which depends on the chemical structure of Raman labels used and the umber of available labels, (b) peak number (designated as M),which depends on the number oflabels used together in a single COIN, and (c) peak height (designated as i), which depends on the ranges of relative peak intensity.

The total number of possible distinguishable Raman signatures (designated as T) may be calculated from the following equation:

$$T = \sum_{k=1}^{M} \frac{L!}{(L-k)!k!} P(i,k)$$

where P(i, k)=$i^k$−i+1, being the intensity multiplier which represents the number of distinct Raman spectra that may be generated by combining k (k=1 to M) labels for a given i value. The multiple organic compounds may be mixed in various combinations, numbers and ratios to make the multiple distinguishable Raman signatures. It has been shown that spectral signatures having closely positioned peaks (15 cm$^{-1}$) may be resolved visually. Theoretically, over a million of Raman signatures may be made within the Raman shift range of 500-2000 cm$^{-1}$ by incorporating multiple organic molecules into COIN as Raman labels using the OCAMF-based COIN synthesis chemistry.

Thus, OCAMF chemistry allows incorporation of a wide range of Raman labels into metal colloids to perform parallel synthesis of a large number of COIN labels with distinguishable Raman signatures in a matter of hours by mixing several organic Raman-active compounds of different structures, mixtures, and ratios for use in the invention methods described herein.

COINs may be used to detect the presence of a particular target analyte, for example, a nucleic acid, oligonucleotide, protein, enzyme, antibody or antigen. The nanoclusters may also be used to screen bioactive agents, i.e. drug candidates, for binding to a particular target or to detect agents like pollutants. Any analyte for which a probe moiety, such as a peptide, protein, oligonucleotide or aptamer, may be designed can be used in combination with the disclosed nanoclusters.

Also, SERS-active COINs that have an antibody as binding partner could be used to detect interaction of the Raman-active antibody labeled constructs with antigens either in solution or on a solid support. It will be understood that such immunoassays can be performed using known methods such as are used, for example, in ELISA assays, Western blotting, or protein arrays, utilizing a SERS-active COIN having an antibody as the probe and acting as either a primary or a secondary antibody, in place of a primary or secondary antibody labeled with an enzyme or a radioactive compound. In another example, a SERS-active COIN is attached to an enzyme probe for use in detecting interaction of the enzyme with a substrate.

Another group of exemplary methods could use the SERS-active COINs to detect a target nucleic acid. Such a method is useful, for example, for detection of infectious agents within a clinical sample, detection of an amplification product derived from genomic DNA or RNA or message RNA, or detection of a gene (cDNA) insert within a clone. For certain methods aimed at detection of a target polynucleotide, an oligonucleotide probe is synthesized using methods known in the art. The oligonucleotide is then used to functionalize a SERS-active COIN. Detection of the specific Raman label in the SERS-active COIN identifies the nucleotide sequence of the oligonucleotide probe, which in turn provides information regarding the nucleotide sequence of the target polynucleotide.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The term "waveguide" refers to a device that controls the propagation of an electromagnetic wave so that the wave is forced to follow a path defined by the physical structure of the guide. Generally speaking, the electric and magnetic fields of an electromagnetic wave have a number of possible arrangements when the wave is traveling through a waveguide. Each of these arrangements is known as a mode of propagation. Optical waveguides are used at optical frequencies. An "optical waveguide" is any structure having the ability to guide optical energy. Optical waveguides may be (a) thin-film deposits used in integrated optical circuits (IOCs) or (b) optical fibers.

The term "optical switch" refers to a switch that enables signals in optical fibers or integrated optical circuits (IOCs) to be selectively switched from one circuit to another. An optical switch may operate by (a) mechanical means, such as physically shifting an optical fiber to drive one or more alternative fibers, or (b) electro-optic effects, magneto-optic effects, or other methods. Slow optical switches, such as those using moving fibers, may be used for alternate routing of an optical transmission path. Fast optical switches, such as those using electro-optic or magneto-optic effects, may be used to perform logic operations. One type of an optical switch is a thin film optical switch, which is a switch having multilayered films of material of different optical characteristics, that is capable of switching transmitted light by using electro-optic, electro-acoustic, or magneto-optic effects to obtain signal switching, and is usually used as a component in integrated optical circuits. Thin-film optical switches may support only one propagation mode.

The term "PIN diode" refers to positive-intrinsic-negative diode. A photodiode with a large, neutrally doped intrinsic region sandwiched between p-doped and n-doped semiconducting regions. A PIN diode exhibits an increase in its electrical conductivity as a function of the intensity, wavelength, and modulation rate of the incident radiation. A PIN diode is also called photodiode.

The terms "spectrum" or "spectra" refer to the intensities of electromagnetic radiation as a function of wavelength or other equivalent units, such as wavenumber, frequency, and energy level.

The term "spectrometer" refers to an instrument equipped with scales for measuring wavelengths or indexes of refraction.

The term "dispersive spectrometer" refers to a spectrometer that generates spectra by optically dispersing the incoming radiation into its frequency or spectral components. Dispersive spectrometers can be further classified into two types: monochromators and spectrographs. A monochromator uses a single detector, narrow slit(s) (usually two, one at the entrance and another at the exit port), and a rotating dispersive element allowing the user to observe a selected range of wavelength. A spectrograph, on the other hand, uses an array of detector elements and a stationary dispersive element. In this case, the slit shown in the figure is removed, and spectral elements over a wide range of wavelengths are obtained at the same time, therefore providing faster measurements with a more expensive detection system.

The term "dispersive element" refers to a component of a dispersive spectrometer that can disperse electromagnetic radiation such a light. Dispersive elements include prisms and gratings.

The term "interferometer" refers to an instrument that uses the principle of interference of electromagnetic waves for purposes of measurement. For example, it could be any of several optical, acoustic, or radio frequency instruments that use interference phenomena between a reference wave and an experimental wave or between two parts of an experimental wave to determine wavelengths and wave velocities, measure very small distances and thicknesses, and calculate indices of refraction.

The term "non-dispersive element" refers to an interferometer that does not disperse electromagnetic radiation in spatial domain but instead creates a phase shift in the electromagnetic radiation.

The term "Fourier transform spectrometer" refers to a spectrometer used for Fourier transform spectroscopy, which is a measurement technique whereby spectra are collected based on the response from a pulse of electromagnetic radiation. It can be applied to variety of types of spectroscopy including infrared spectroscopy (FTIR), nuclear magnetic resonance, and electron spin resonance spectroscopy. Fourier transform spectroscopy can be more sensitive and has a much shorter sampling time than conventional spectroscopic techniques. For example, in a conventional (or "continuous wave") nucleic magnetic resonance spectrometer, a sample is exposed to electromagnetic radiation and the response (usually the intensity of transmitted radiation) is monitored. The energy of the radiation is varied over the desired range and the response is plotted as a function of radiation energy (or frequency). At certain resonant frequencies characteristic of the specific sample, the radiation will be absorbed resulting in a series of peaks in the spectrum, which can then be used to identify the sample. (In magnetic spectroscopy, the magnetic field is often varied instead of the frequency of the incident radiation, though the spectra are effectively the same as if the field had been kept constant and the frequency varied. This is largely a question of experimental convenience.) Instead of varying the energy of the electromagnetic radiation, Fourier Transform nucleic magnetic resonance spectroscopy exposes the sample to a single pulse of radiation and measures the response. The resulting signal, called a free induction decay, contains a rapidly decaying composite of all possible frequencies. Due to resonance by the sample, resonant frequencies will be dominant in the signal and by performing a mathematical operation called a Fourier transform on the signal the frequency response can be calculated. In this way the Fourier transform nucleic magnetic resonance spectrometer can produce the same kind of spectrum as a conventional spectrometer, but generally in a much shorter time.

The term "optical bench" refers to an apparatus for observation and measurement of optical phenomena. For example, it could be an apparatus such as a special table or rigid beam, for the precise positioning of light sources, screens, and optical instruments used for optical and photometric studies, having a ruled bar to which these devices can be attached and along which they can be readily adjusted.

The term "interferogram" or "Fourier transform spectrum" used herein means the detector response as a function of the optical path length difference caused by the interference of electromagnetic radiation.

The embodiments of this invention relate to an analyzer that would function as a miniaturized Fourier transforming spectrometer comprising an interferometer comprising waveguides. The analyzer could comprise an interferometer, a detector and a microprocessor, wherein the analyzer does not contain a spectrometer having a dispersive grating, the interferometer is to create a phase shift in an original spectrum of electromagnetic radiation emitted from a sample and Fourier transform the original spectrum to a Fourier transform spectrum, the detector is to detect a characteristic of the Fourier transform spectrum, and the microprocessor comprises software or a hardware to inverse transform the Fourier transform spectrum and reproduce the original spectrum. After passing through the MZI, the intensity of the electromagnetic radiation is measured as a function of phase shift. The phase is varied to obtain the Fourier transform of the spectrum. The characteristic could be wavelength, frequency, wave number, amplitude or any other property of the spectrum of electromagnetic radiation (e.g., light).

Figure 2:
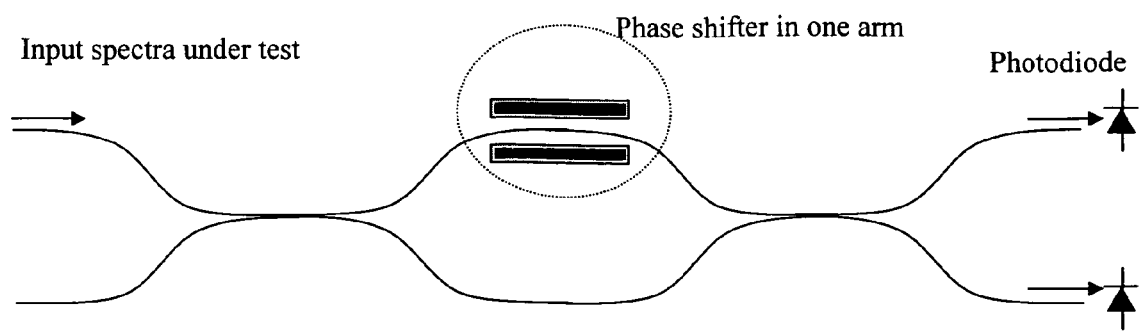
FIG. 2 shows an embodiment of a Mach-Zehnder interferometer (MZI) of this invention.

One embodiment of the invention could be an analyzer having a Mach-Zehnder interferometer (FIG. 2), which is functionally similar to the Michelson interferometer of FIG. 1. However, instead of creating the phase delay by changing the path length difference as in the Michelson interferometer, in Mach-Zehnder interferometer (MZI) a variable index-of-refraction material could be put into one of the two beam paths. By carefully controlling the index-of-refraction of the material, different interference fringes could be formed, which can be recorded by a single channel detector, for example. The recorded signal could be computed (inverse Fourier transformed) by a microprocessor to obtain the spectrum. The above embodiments of the analyzer would not require a spectrometer having a dispersive grating or having any moving parts.

An alternative embodiment could be a miniaturized Michelson interferometer with a micro-electro-mechanical-system (MEMS) based moving arm. Multiple folded mirrors can be used to increase the path length difference. Optionally, separated waveguides with a reference light source may pass through the same phase-shifter to monitor the phase shifting accurately.

In one embodiment of the analyzer of the invention, a beam emitted from a beam emitter, e.g. an Argon-ion laser, could be filtered for monochromaticity and directed by a system of mirrors to a focusing/collecting lens. The beam could be focused onto the sample and the scattered light from the sample could be allowed to passes through a set of lens into a first stage of the analyzer. Preferably, the sample should be oriented such that the specular reflection from the sample passes outside of the collection lens—otherwise, the reflection of the beam striking the sample could potentially damage the detector, which could be designed to be sensitive enough to even detect weak Raman signals emitted by the sample.

The analyzer of the embodiments of the invention could generally be separated into four stages. The first stage, which is optional, could include optical elements (collecting lenses, for example) to collect and concentrate the electromagnetic radiation emitted from the sample.

In one embodiment, the second stage is an interferometer comprising optical waveguides having at least two arms, for example, with input and output focusing mirrors. The incoming signal from the collecting lenses could be passed through a first pair of arms of the optical waveguide, wherein a variable index-of-refraction material could be put into one of the two beam paths of the first pair of arms of the optical waveguide. By carefully controlling the index-of refraction of the material a varying phase shift could be introduced into one of the arms of the MZI and different interference fringes could be formed at the output of the interferometer. This light can be refocused and the light contains information in the form of the Fourier transform of the spectrum of light emitted by the sample.

This refocused light is sent out to the third stage, which is the detector, preferably a single detector. The detector converts an optical signal of the characteristic of the Fourier transform spectrum to an electrical signal. The detector could be a charge coupled analyzer, a transducer or a photodiode.

The phase/intensity information as electrical signals generated by the detector is then read to a microprocessor, which is the fourth stage of the analyzer. The microprocessor contains software or a hardware to inverse Fourier transform the Fourier transform spectrum into the original spectrum of light emitted by the sample, which could be a frequency/intensity or wavelength/intensity spectrum such as a Raman spectrum, for example.

The data from the microprocessor could come out as an intensity/frequency plot of a spectrum. To resolve a peak of a certain width of the spectrum, the resolution of the analyzer could be smaller than the peak width.

As the analyzer in its parts or as a whole could have a wavelength (or frequency) dependent transmittance, the actual spectrum displayed is a product of the spectrometer frequency response with the actual spectrum of the scattered light. Thus, to know not only the energies of particular excitations, for example, Raman-active excitations, but also the relative magnitudes of the scattering at different frequencies, it would be desirable to calibrate the analyzer response to a source with a known spectrum. Thus, one could use a traceable standard lamp or a spectrum from a well-characterized piece of luminescent glass.

The embodiments of the analyzer of this invention could be directed, for example by passing through a filter such as an optical filter, to substantially exclude IR signals and include substantially only Raman signals, for example, that are detected by a detector. This filter can be integrated directly with the MZI being used as the Fourier transform spectrometer. As an example of such a filter, notch filters can be fabricated by etching a surface corrugation onto a silicon waveguide, these filters are commonly called Bragg filters. By cascading multiple filters together high pass and low pass filters may be formed which could optimize the signal to noise of the entire system. Other examples of filter types include ring resonators, etalons or MZI interferometers.

The analyzer of the embodiments of the invention could further include an edge filter, which could be located prior to the interferometer or between the interferometer and the detector. The edge filter of the embodiments of the invention could be of long or short wave pass types produced by established multi-layer thin film coating techniques from all-dielectric materials. This manufacturing method allows a high degree of flexibility in edge position coupled with low absorption losses to be achieved, compared with bulk glass or dye filter types. Edges for long and short wave pass types can be set anywhere in the 400 nm to 5000 nm wavelength range. The filter wavelength, regardless of type, is generally specified as the 5% transmission point as shown in FIG. 3. Tolerances on this position are generally held to better than +/−2% of cut-on/off wavelength (which are defined at the 5% transmission), although this may be improved by selection. In a long wave pass type edge filter, light of lower wavelength is blocked while light of higher wavelength is transmitted through the edge filter. In a short wave pass type edge filter, light of higher wavelength is blocked while light of lower wavelength is transmitted through the edge filter. The rate of change of transmission of the edge could be approximately 5%. This is generally sufficient for most applications, although steeper edges, tending towards 2% or less, can be produced and may be preferable. Suppression of unwanted transmission 'leaks' outside the pass band could be generally better than <0.1% for the edge filters of the embodiments of the invention. Rejection levels of 0.01% or more can be achieved by the embodiments of the invention. This level of blocking performance, coupled with high average transmissions, could ensure excellent system signal to noise ratios.

A wide range of substrate materials and sizes could be used for the substrate of the edge filter. Some possible sizes of the edge filter include as 12.5 mm, 22 mm and 25 mm diameter. The edge filter can generally be operated in a temperature range of 50° C. to 100° C.

Figure 4:
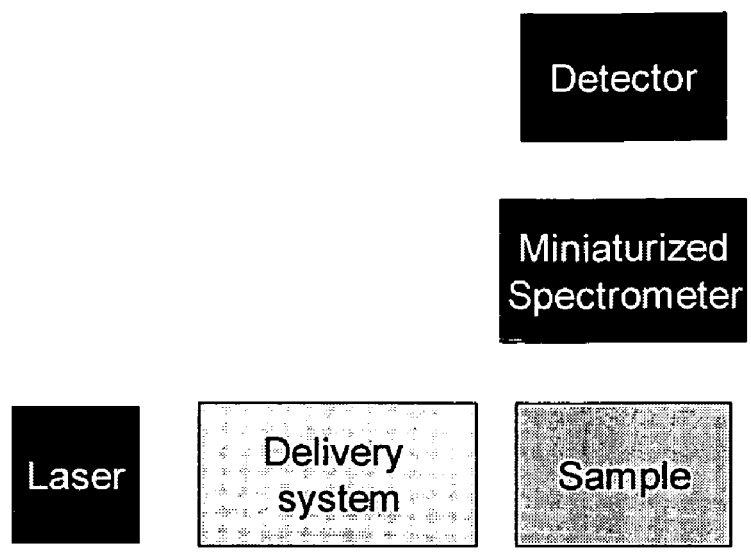
FIG. 4 shows the basic architecture of Raman-on-chip (ROC).

Another embodiment of this invention relates to a Raman analyzer comprising an interferometer, wherein the Raman analyzer contains no dispersive grating or moving parts and has an ability to analyze a Raman signal. The basic architecture of the Raman analyzer, particularly, a Raman-on-chip (ROC) analyzer is shown in FIG. 4. Referring to FIG. 4, the ROC could comprise a beam emitter, preferably having a diode laser as a light source. Diode lasers can generate light from around visible (~630 nm) to infrared (e.g. 1550 nm). Additionally diode pumped solid state lasers (typically 532 nm) could also be used as the light source of the beam emitter. The ROC could further comprise a delivery system to deliver the laser beam to the sample. When the laser beam strikes the sample, the sample emits radiation, including Raman signals, which are collected and delivered to a miniaturized spectrometer, which is preferably an interferometer comprising two arms to pass a portion of the original spectrum through each of the two arms, wherein one of the two arms comprises a phase shifter comprising a variable index material. The Raman analyzer could further comprise a detector, wherein the detector could be a charge coupled analyzer, a transducer or a photodiode. The Raman analyzer could further comprise a microprocessor comprising software or a hardware to inverse Fourier transform a Raman spectrum.

The ROC could have multiple channels such that it can be used in composite organic-inorganic nanoclusters (COIN) applications, for example. The spectrum of COIN (FIG. 5) shows that multiple channels (~40 channels with 1 nm width) would be required to identify the COIN types in samples. Additional details on how the ROC could be used in COIN applications are provided below.

In the embodiments of this invention, chemical species could be detected remotely by Raman lidar-based analyzer using optical signals from electromagnetic radiation including visible light. The analyzers of the embodiments of the invention capture Raman signals from a sample resulting from Raman scattering from the sample.

Raman scattering is a powerful light scattering technique used to diagnose the internal structure of molecules and crystals. In a light scattering experiment, light of a known frequency and polarization is emitted from a sample. The scattered light is then analyzed for frequency and polarization. Raman scattered light is frequency-shifted with respect to the excitation frequency, but the magnitude of the shift is independent of the excitation frequency. This "Raman shift" is therefore an intrinsic property of the sample.

Because Raman scattered light changes in frequency, the rule of conservation of energy dictates that some energy is deposited in the sample. A definite Raman shift corresponds to vibrational energy of the sample (i.e. the energy of a free vibration of a molecule). In general, only some vibrational bands of a given molecule are "Raman active," that is, only some may take part in the Raman scattering process. Hence the frequency spectrum of the Raman scattered light maps out part of the vibrational spectrum. Other spectroscopic techniques, such as IR absorption, could be used to map out the non-Raman active excitations.

Additional information, related to the spatial form of the excitation, derives from the polarization dependence of the Raman scattered light. The shape of an excitation in a material, for example a vibration pattern of the atoms in a molecule, and the polarization dependence of the scattering, are determined by the equilibrium structure of the material through the rules of group theory. By this route one gleans valuable and unambiguous structural information from the Raman polarization dependence.

Raman spectroscopy technique of the embodiments of the invention is based upon the Raman effect which may be described as the scattering of light from a gas, liquid or solid with a shift in wavelength from that of the usually monochromatic incident radiation.

Raman spectroscopy provides information about molecular vibrations that can be used for sample identification and quantification. The technique of the embodiments of the invention involves shining a monochromatic light (i.e., laser) on a sample. Laser-produced, monochromatic light of ultra-violet, visible, or infrared frequency could be used as the light source. In some embodiments of the Raman spectroscopy technique of the embodiments of the invention, visible lasers could used (e.g., Ar+, Kr+, Nd:YAG, He—Ne, diode) to create molecular vibration to high-energy "virtual" states of excitation.

The light interacts with the sample and part of it is transmitted, part of it is reflected, and part of it is scattered. The scattered light is detected by one or more detectors. The majority of the scattered light is of the same frequency as the excitation source; this is known as Rayleigh or elastic scattering. A very small amount of the scattered light (less, than 1%, but more likely about $10^{-5}$ of the incident light intensity), called Raman or inelastic scattering, has frequencies different from that of the incident light due to interactions between the incident electromagnetic waves and the vibrational energy levels of the molecules in the sample.

That is, the scattered radiation is examined spectroscopically, not only is light of the exciting frequency, $V_0$, observed (Rayleigh scattering), but also some weaker bands of shifted frequency are detected. Moreover, while most of the shifted bands are of lower frequency $v_0-v_i$, there are some at higher frequency, $v_0 + v_i$. By analogy to fluorescence spectrometry, the former are called Stokes bands and the latter anti-Stokes bands. The Stokes and anti-Stokes bands are equally displaced about the Rayleigh band; however, the intensity of the anti-Stokes bands is much weaker than the Stokes bands and they are seldom observed. The scattered radiation produced by the Raman effect contains information about the energies of molecular vibrations and rotations, and these depend on the particular atoms or ions that comprise the molecule, the chemical bonds connect them, the symmetry of their molecule structure, and the physico-chemical environment where they reside.

Plotting the intensity of this "shifted" light versus frequency results in a Raman spectrum of the sample. The Raman spectra could also be plotted as intensity versus the difference in frequency of the incident light and scattered light such that the Rayleigh band lies at 0 cm$^{-1}$ and the Raman band lie on both sides of the Rayleigh band. On this scale, the band positions could lie at frequencies that correspond to the energy levels of different functional group vibrations. The Raman spectrum can thus be interpreted similar to the infrared absorption spectrum.

The vibrational Raman effect is especially useful in studying the structure of the polyatomic molecule. If such a molecule contains N atoms it can be shown that there could be 3N-6 fundamental vibrational modes of motion only (3N-5 if the molecule is a linear one). Those which are accompanied by a change in electric moment can be observed experimentally in the infrared. The remaining ones, if occurring with a change in polarizability, could be observable in the Raman effect. Thus both kinds of spectroscopic measurements could be applied in a complete study of a given molecule.

Like infrared spectrometry, Raman spectrometry is a method of determining modes of molecular motion, especially the vibrations, and their use in analysis is based on the specificity of these vibrations. The methods are predominantly applicable to the qualitative and quantitative analysis of covalently bonded molecules rather than to ionic structures. Nevertheless, they can give information about the lattice structure of ionic molecules in the crystalline state and about the internal covalent structure of complex ions and the ligand structure of coordination compounds both in the solid state and in solution.

Both the Raman and the infrared spectrum yield certain description of the internal vibrational motion of the molecule in terms of the normal vibrations of the constituent atoms. However, IR absorption and Raman scattering are governed by completely different selection rules. Infrared bands arise from an interaction between light and the oscillating dipole moment of a vibrating molecule. Raman bands arise from an oscillation induced dipole caused by light waves interacting with the polarizability ellipsoid of a vibrating molecule. (It is common to describe the polarizability ellipsoid as the shape of the electron cloud around the molecule). Thus, symmetric stretches, vibrations involving multiple bonds, and vibrations of heavier atoms typically give rise to strong bands in the Raman spectrum. Asymmetric molecules could have bands at similar frequencies in both the infrared and Raman spectra, but their relative intensities could be very different. In most cases, a chemical species could have strong, indicative bands in both its Raman and IR spectra but they may not coincide.

Neither Raman nor IR spectra alone might give a complete description of the pattern of molecular vibration, and, by analysis of the difference between the Raman and the infrared spectrum, additional information about the molecular structure can sometimes be inferred. Physical chemists have made extremely effective use of such comparisons in the elucidation of the finer structural details of small symmetrical molecules, such as methane and benzene, but the mathematical techniques of vibrational analysis are not yet sufficiently developed to permit the extension of these differential studies to the Raman and infrared spectra of the more complex molecules that constitute the main body of both organic and inorganic chemistry.

Raman spectra are very specific, and chemical identifications can be performed by using search algorithms against digital databases. As in infrared spectroscopy, band areas are proportional to concentration, making Raman amenable to quantitative analysis. In fact, because Raman bands are inherently sharper than their infrared counterparts, isolated bands are often present in the spectrum for more straight-forward quantitative analysis. By the technique of the embodiments of the invention, one can use Raman alone, or in combination with IR spectra, in two ways. At the purely empirical level they provide "fingerprints" of the molecular structure and, as such, permit the qualitative analysis of individual compounds, either by direct comparison of the spectra of the known and unknown materials run consecutively, or by comparison of the spectrum of the unknown compound with catalogs of reference spectra. By comparisons among the spectra of large numbers of compounds of known structure, it has been possible to recognize, at specific positions in the spectrum, bands which can be identified as "characteristic group frequencies" associated with the presence of localized units of molecular structure in the molecule, such as methyl, carbonyl, or hydroxyl groups. Many of these group frequencies differ in the Raman and infrared spectra.

Thus, by the Raman spectroscopy technique of the embodiments of the invention, wavelengths and intensities of the scattered light can be used to identify functional groups of molecules because each compound has its own unique Raman spectrum which can be used as a finger print for identification. It has found wide application in the chemical, polymer, semiconductor, and pharmaceutical industries because of its high information content.

Raman spectra, not only provides a chemical fingerprint, but also provides additional information including:

Identification of minerals and organic substances. From the identities of minerals, we know the chemical formulas and the arrangements of the atoms within them. Thus, we know whether the mineral was a carbonate, sulfate, phosphate, silicate, oxide, sulfide, hydroxide, etc. In some cases for which chemical compositions can vary, e.g., in the ratio of iron to magnesium ions, we can determine the cation ratio Easy sampling of solids, powders, gels, liquids, slurries, and aqueous solutions No sample preparation Sampling through windows, transparent containers, blister packs, or by immersion Remote sampling using fiber optic probes (up to 100 meters)

Sharp spectral peaks for quantitative and qualitative analysis

Identification of phases (mineral inclusions, daughter minerals in fluid inclusions, composition of the gas phase in inclusions)

Anions in the fluid phase ($CO_3^{2-}$, $HCO_3^{31}$, $PO_4^{3-}$, $BO_4^{3-}$, $SO_4^{2-}$, $HS^-$, $OH^-$)

Identification of crystalline polymorphs (sillimanite, kyanite, andalusite and others)

Measurement of mid-range order in solids

Measurement of orientation

Measurement of stress

High-pressure and high-temperature in situ studies

Phase transition and order-disorder transitions in minerals (quartz, graphite)

Water content of silicate glasses and minerals

Speciation of water in glasses

Raman scattering technique of the embodiments of the invention is a spectroscopic technique that is complementary to infrared absorption spectroscopy. Raman offers several advantages over mid-IR and near-IR spectroscopy, including:

Little or no sample preparation is required

Water is a weak scatterer—no special accessories are needed for measuring aqueous solutions Water and $CO_2$ vapors are very weak scatterers-purging is unnecessary Inexpensive glass sample holders are ideal in most cases Fiber optics (up to 100's of meters in length) can be used for remote analyses Since fundamental modes are measured, Raman bands can be easily related to chemical structure Raman spectra are "cleaner" than mid-IR spectra-Raman bands are narrower, and overtone and combination bands are generally weak The standard spectral range reaches well below 400 $cm^{-1}$, making the technique ideal for both organic and inorganic species Raman spectroscopy can be used to measure bands of symmetric linkages which are weak in an infrared spectrum (e.g. —S—S—, —C—S—, —C=C—)

Raman scattering is, as a rule, much weaker than Rayleigh scattering (in which there is no frequency shift) because the interactions which produce Raman scattering are higher order. Therefore, it is preferred to use an intense source which is as monochromatic as possible—a laser with a narrow linewidth is usually used—and the collected light should be carefully filtered to avoid the potentially overwhelming Rayleigh signal. Other potentially large sources of non-Raman signal include fluorescence (the decay of long-lived electronic excitations) and of course light from ambient sources. Fluorescence can be particularly pernicious to a Raman measurement because the fluorescence signal is also shifted from the laser frequency, and so can be much more difficult to avoid. Note that although the fluorescence spectrum is shifted from the laser frequency, the fluorescence shift depends on the laser frequency whereas the Raman shift does not.

As an analytical technique, Raman spectroscopy has major advantages, the most important being the ease of sample preparation and the rich information content. Raman is essentially a light scattering technique, so all that is required for collection of a spectrum is a means to place the sample into the excitation beam and collecting the scattered light. Therefore in the embodiments of the invention, there are few concerns with sample thickness (as in transmission analyses) and little contribution from the ambient atmosphere, so there is no need for high-vacuum or desiccated sample holders. Glass, water and plastic packaging each have very weak Raman spectra, making the technique easy to use. Often, samples of the embodiments of the invention can be analyzed directly inside the glass bottle or plastic bag without opening the package and risking contamination. Advantageously over infrared spectroscopy, aqueous samples are readily analyzed without the need to remove water, and because ambient humidity is not a problem, there is no need to purge the instrument.

No two molecules would give exactly the same Raman spectrum, and the intensity of the scattered light is related to the amount of material present. This makes it easy to obtain both qualitative and quantitative information about the sample, allowing for spectral interpretation, library searching, data manipulations and the application of quantitative analysis computer methods.

Raman spectroscopy by the embodiment of this invention is generally non-destructive. Unlike IR- or other spectroscopy techniques, there could be no need to dissolve solids, press pellets, compress the sample against optical elements or otherwise alter the structure of the sample in the embodiments of the invention. Raman spectrometers of the embodiments of the invention could employ one of two technologies for the collection of spectra: (1) Dispersive Raman spectroscopy and (2) Fourier transform Raman spectroscopy. Each technique has its unique advantages and is suited to specific analyses. Raman spectroscopy may also be performed on chemical species in the vapor phase without having to chemically fix the species. Some embodiments of the invention also include microscopic examination of the samples using Raman microscopes and Raman confocal microscopes to analyze for texture.

Yet another embodiment of the invention relates to a method for analyzing a sample, comprising striking the sample with a beam to produce an original spectrum of electromagnetic radiation, creating a phase delay in the original spectrum, transforming the original spectrum into a Fourier transform spectrum, detecting a characteristic of the Fourier transform spectrum, and transforming the Fourier transform spectrum into the original spectrum. Preferably, the creating the phase delay in the original spectrum and the transforming the original spectrum into the Fourier transform spectrum are performed by an interferometer, the detecting a characteristic of the Fourier transform spectrum is performed by a detector, and the transforming the Fourier transform spectrum into the original spectrum is performed by a microprocessor.

Fabrication of the MZI and ROC Analyzers

The Fourier transform spectrometer with MZI and ROC analyzers can be fabricated using common semi-conductor fabrication techniques. As an example a silicon wafer could be used as the starting material. An oxide layer could be grown to be used as the bottom cladding of the waveguide. SiON could then be deposited to be used as the waveguide core. This could then have waveguides patterned onto it using wet or dry chemical etching. Control of the index of the MZI arms could be done using the thermo-optic effect by preferentially heating the MZI arms with heaters deposited onto the waveguide. Filters could be integrated onto the waveguide by etching the upper surface or sidewall of the waveguide, or by varying the refractive-index of the waveguide as a function of position. An integrated photodetector could be formed by fabricated a silicon PIN diode on the same substrate as the spectrometer in a way similar to obtaining planar optical devices that is known to persons of ordinary skill in this art.

Fabrication of Multiple Mach-Zehnder Interferometers with Array Detector

Figure 10:
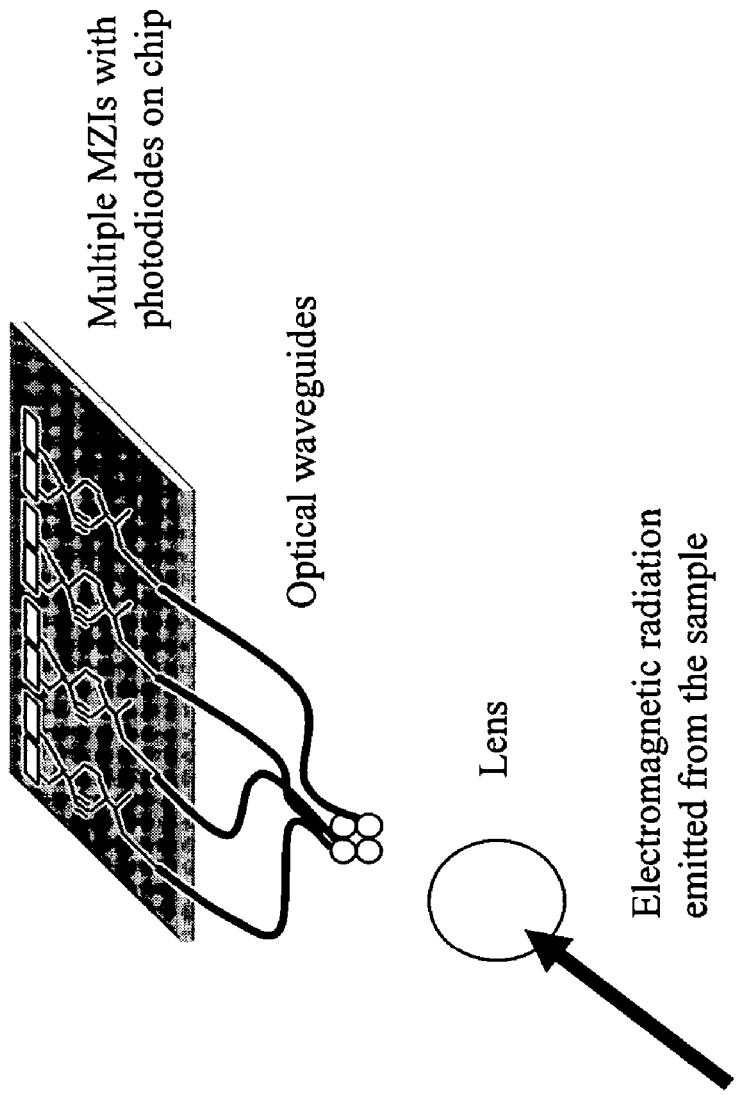
FIG. 10 schematically illustrates multiple Mach-Zehnder interferometers with an array detector.

Multiple Mach-Zehnder interferometers could be combined into an multiple MZIs with photodiodes on a chip as shown in FIG. 10. At one end, each or some of the MZIs of the multiple MZIs could be connected to fiber optic cables which deliver electromagnetic radiation such as light to the MZI. At the other end, each or some of the MZIs of the multiple MZIs could be connected to an array detector having a plurality of detectors or a single detector having multiple channels. Each channel could be for detecting electromagnetic radiation such as light arriving from different location or for detecting electromagnetic radiation such as light having different characteristics such as different wavelengths.

Applications of the MZI and ROC analyzers

Figure 5:
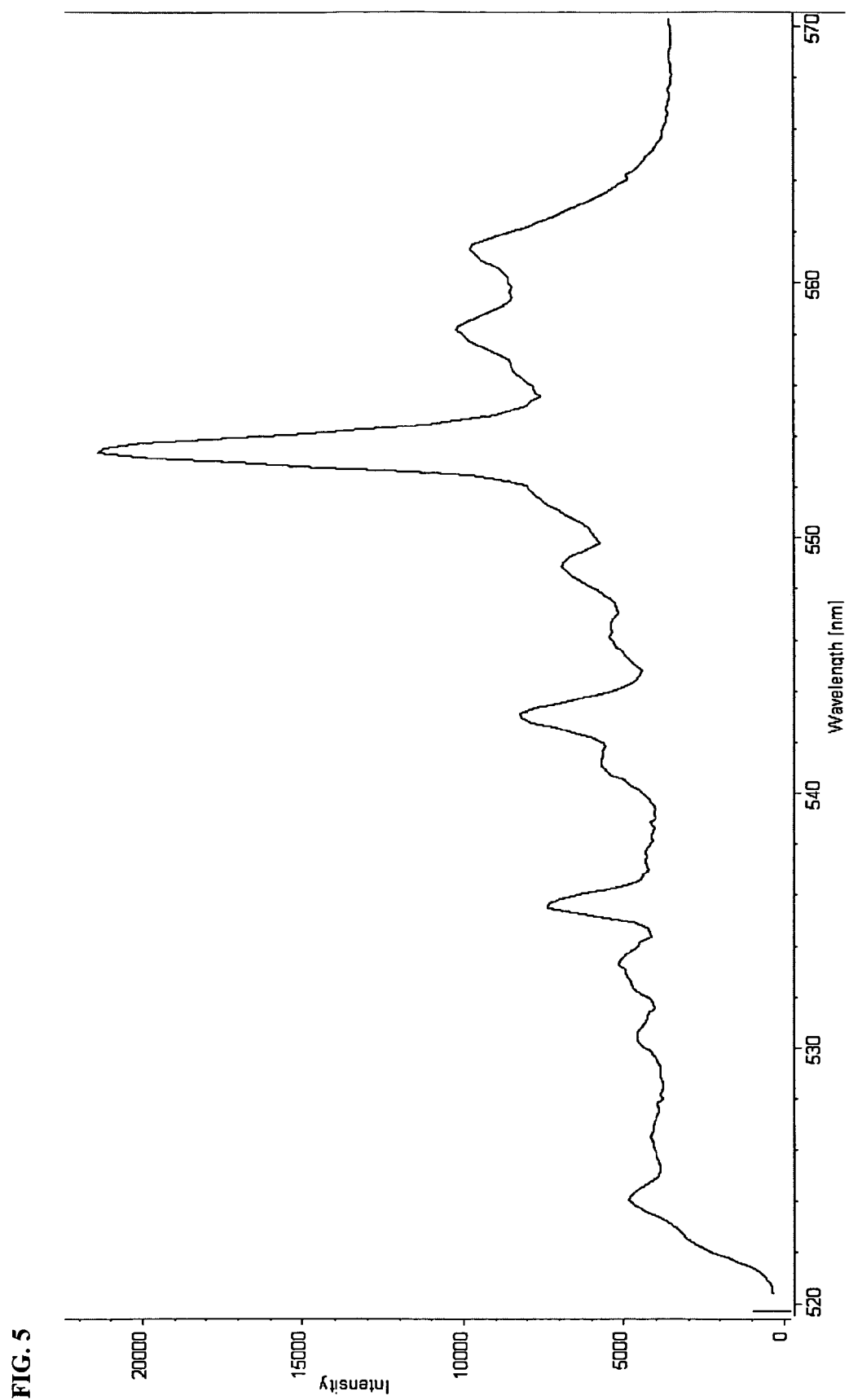
FIG. 5 shows the Raman spectrum of COIN.

The embodiments of the MZI and ROC analyzers could be used in Composite organic-inorganic nanoclusters (COIN) applications. The exemplary spectrum of COIN is shown in FIG. 5, showing that a MZI or ROC analyzer having multiple channels (~40 channels with 1 nm width) would be required to identify the COIN types in samples.

Figure 6:
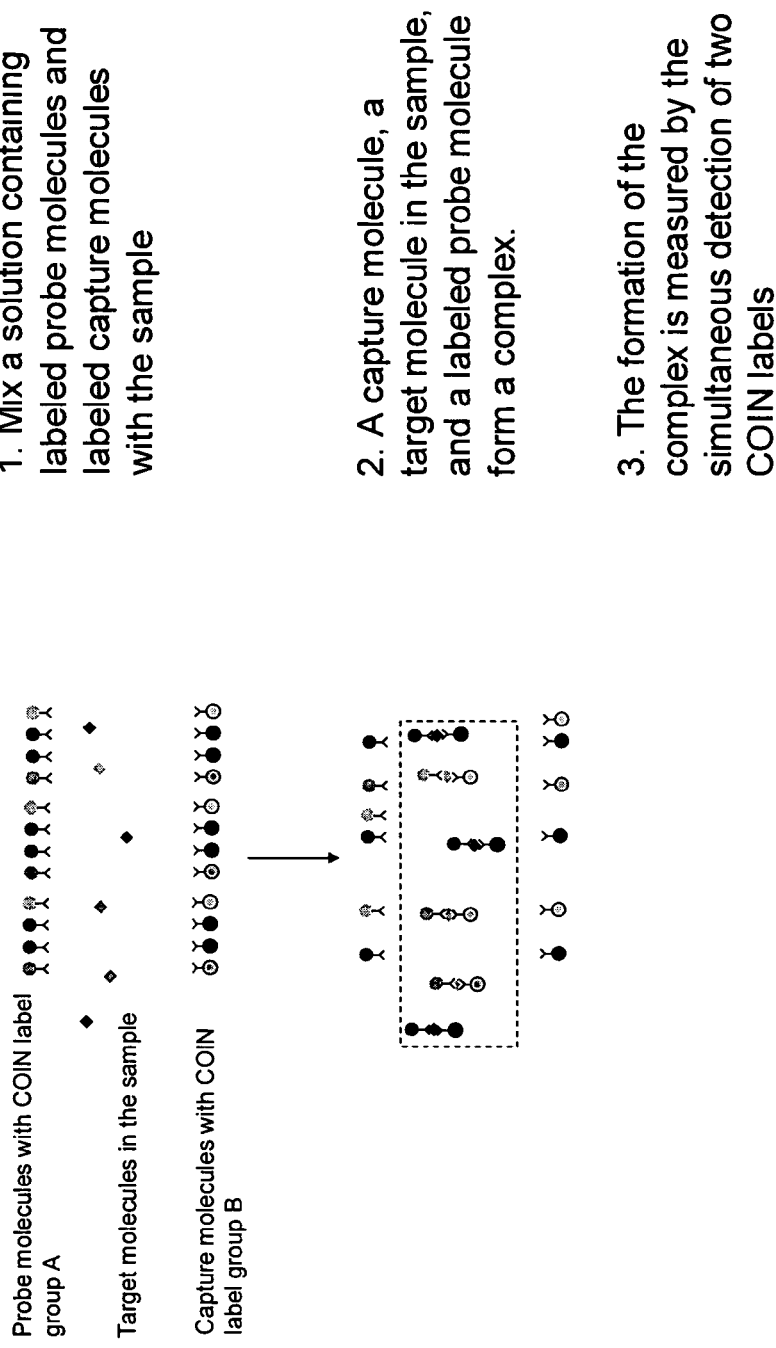
FIG. 6 shows the sample preparation method for a microfluid channel based MZI or ROC analyzer systems.

One embodiment of the applications of the MZI and ROC analyzers could be a micro-fluid channel based system. The method steps of for this embodiment of the application are shown in FIGS. 6 and 7. Even though FIGS. 6-9 state "Raman-on-chip," the embodiments of FIGS. 6-9 are equally applicable to the MZI and ROC analyzers. In particular, the steps are as follows:
1. Mix a solution containing labeled probe molecules and labeled capture molecules with the sample to be analyzed. Both the probe and capture molecules have a COIN label. The sample could be a polymer, a nanomaterial, a carbon nanotube, a nucleotide, or a biomaterial such a peptide, a protein, a ligand, a receptor, a sequence, DNA, RNA, etc.
2. Form a complex, which might involve hybridization, of the COIN labeled capture molecule, a target molecule of the sample and the COIN labeled probe molecule.
3. Detect the complex by simultaneous detection of two COIN labels attached to the complex, which contains the first and second COIN labels of the probe molecule and the target molecule, respectively.

The detection methodology is shown schematically in FIG. 7. The laser light is focused into an optical waveguide, and is delivered to the sample which flows through a micro-fluid channel. The sample scatters light and emits radiation, including Raman emission. The radiation from the sample would be collected by an optical waveguide based spectrometer such as that shown in FIG. 2, passed through the MZI or ROC and the output of the MZI or ROC would be detected by a detector.

Figure 9:
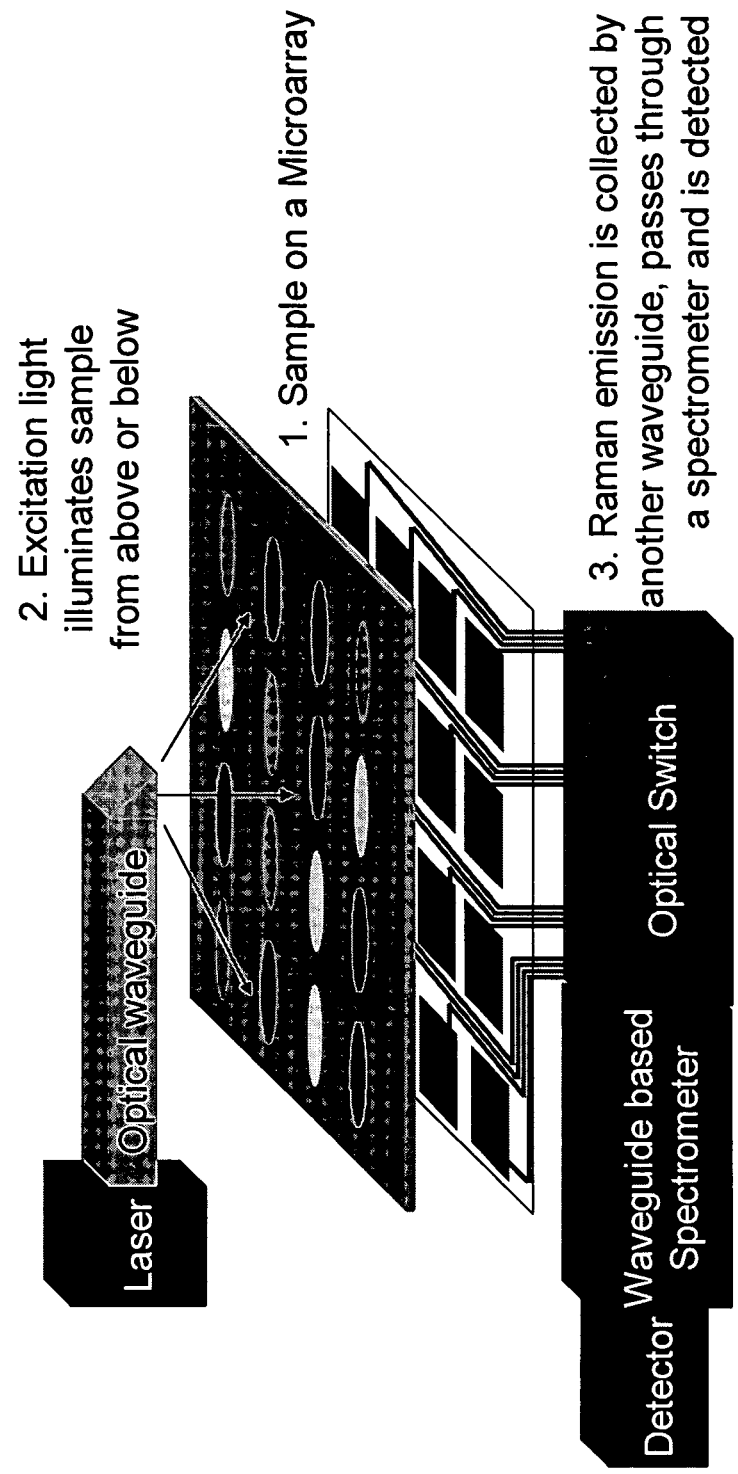
FIG. 9 shows the detection methodology for a micro-array based MZI or ROC analyzer systems.

In another embodiment, if the sample is spotted onto a substrate in an array format, a MEMS scanning mirror can be placed to scan the multiple spots on the substrate. Alternatively, the laser light can be coupled to multiple waveguides through an optical switch, and each waveguide can be positioned to each spot on the substrate. The method steps of for this embodiment of the application are shown in FIGS. 8 and 9. In particular, the steps are as follows:
1. Introduce the sample and the COIN labeled probe molecules on a substrate of a microarray having spots containing capture molecules (which may or may not be labeled). The sample could be a polymer, a nanomaterial, a carbon nanotube, a nucleotide, or a biomaterial such a peptide, a protein, a ligand, a receptor, a sequence, DNA, RNA, etc.
2. Form a complex, which might involve hybridization, of the capture molecule, a target molecule of the sample and the COIN labeled probe molecule.
3. Detect the complex by detection of one COIN label (or simultaneous detection of two COIN labels if the capture molecule is a COIN labeled capture molecule) attached to the complex.

The detection methodology to detect the sample on the microarray is shown schematically in FIG. 9. The laser light through an optical waveguide is focused on the microarray and the complex on microarray could be illuminated from either above or below the microarray. The complex emits its own signature spectrum comprising a Raman signal. The signature spectrum is collected by an optical waveguide based spectrometer such as that shown in FIG. 2, passed through the MZI or ROC and the output of the MZI or ROC would be detected by a detector.

In the embodiments of the invention such as the two embodiments described above with reference to FIGS. 6-9, the sample receives the laser light, and emits a unique spectrum of light specific to the type of COIN. A miniaturized spectrometer and detector is placed to analyze the spectrum of the emitted light by a miniaturized spectrometer and detector system such as that shown in FIG. 2, for example.

The embodiments of the invention could further include a sample collection device for collecting the sample that has to be analyzed by the analyzer of the embodiments of the invention. The sample collection device could include suction and sample concentration devices. For example, a solid, liquid or gaseous sample could be sucked into a sample collection device that produces a known background signal. Then, the sample could be concentrated within the sample collection device. For example, a gas could be cooled to create condensate in the sample collection device. By concentrating the sample in the sample collection device, it could reduce the analysis time, particularly for a gaseous sample.

While only certain features of the invention have been illustrated and described herein, many modifications and changes will occur to those skilled in the art. It is, therefore, to be understood that the appended claims are intended to cover all such modifications and changes as fall within the true spirit of the invention.

The analyzer could also be used for therapeutic materials development, i.e., for drug development and for biomaterial studies, as well as for biomedical research, analytical chemistry, high throughput compound screening, and bioprocess monitoring. Yet other applications of the analyzer could be for developing new materials, particularly nanomaterials for many purposes including, but not limited to corrosion resistance, battery energy storage, electroplating, low voltage phosphorescence, bone graft compatibility, resisting fouling by marine organisms, superconductivity, epitaxial lattice matching, or chemical catalysis.

It is further contemplated that analyzer of the embodiments of the invention could be used to develop screening methods for testing materials. That is, reagents electrochemically generated by an electrode on a die could be used to test the physical and chemical properties of materials. For example, the analyzer could be used for testing corrosion resistance, electroplating efficiency, chemical kinetics, superconductivity, electro-chemiluminescence and catalyst lifetimes.

The embodiments of this invention have yet other several practical uses. For example, one embodiment of the invention allows molecules and nanomaterials detection/analysis based on the electrical readout of specific captured Raman signals (fingerprints) of molecules and nanomaterials. Another embodiment of the invention has potential applications for nanomaterials study to be used in electronic devices (transistors and interconnects) as well as well as for detection of bio-species (DNA, protein, viruses etc.) for molecular diagnostics, homeland security, drug discovery and life science R&D work.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. An analyzer comprising an interferometer, a detector and a microprocessor, wherein the analyzer does not contain a spectrometer having a dispersive element, the interferometer is to create a varying phase shift in an original spectrum of electromagnetic radiation emitted from a sample and Fourier transform the original spectrum to a Fourier transform spectrum, the detector is to detect a characteristic of the Fourier transform spectrum, and the microprocessor comprises software or a hardware to inverse transform the Fourier transform spectrum and reproduce the original spectrum.

2. The analyzer of claim 1, wherein said detector has an ability to convert an optical signal of the characteristic of the Fourier transform spectrum to an electrical signal.

3. The analyzer of claim 1, wherein the electromagnetic radiation comprises light.

4. The analyzer of claim 1, further comprising a beam emitter that emits a beam that strikes the sample.

5. The analyzer of claim 4, wherein the emitter beam comprises laser.

6. The analyzer of claim 1, further comprising optical elements to collect and concentrate the electromagnetic radiation emitted from the sample.

7. The analyzer of claim 1, wherein the detector is a single detector.

8. The analyzer of claim 1, wherein the detector is a charge coupled analyzer, a transducer or a photodiode.

9. The analyzer of claim 1, wherein the electromagnetic radiation emitted from the sample comprises a Raman signal, an infrared (IR) signal, a fluorescence signal, or a luminescence signal.

10. The analyzer of claim 1, wherein the interferometer comprises two arms to pass a portion of the original spectrum through each of the two arms.

11. The analyzer of claim 10, wherein one of the two arms comprises a phase shifter.

12. The analyzer of claim 11, wherein the phase shifter comprises a variable index material.

13. The analyzer of claim 1, wherein the interferometer comprises a MEMS based device, an optical bench, a wafer having optical structures, an optical splitter or an optical waveguide.

14. The analyzer of claim 13, wherein the optical splitter or the optical waveguide comprises optical fibers coupled to each other to form the optical splitter or the optical guide.

15. The analyzer of claim 13, wherein the optical bench comprises a MEMS based moving arm.

16. A Raman analyzer comprising an interferometer built on a chip, wherein the Raman analyzer contains no dispersive element or moving parts and has an ability to analyze a Raman signals,
wherein the interferometer comprises two arms to pass a portion of an original spectrum through each of the two arms,
wherein one or more of the two arms comprises a phase shifter, wherein the phase shifter comprises a variable index material.

17. The Raman analyzer of claim 16, wherein the chip comprises a semiconductor material.

18. The Raman analyzer of claim 16, further comprising a detector.

19. The Raman analyzer of claim 18, wherein the detector comprises a charge coupled analyzer, a transducer or a photodiode.

20. The Raman analyzer of claim 16, further comprising a microprocessor comprising software or a hardware to inverse Fourier transform a Raman spectrum.

* * * * *